US006455533B1

(12) United States Patent
Fanara et al.

(10) Patent No.: US 6,455,533 B1
(45) Date of Patent: *Sep. 24, 2002

(54) PHARMACEUTICAL COMPOSITIONS FOR ORAL ADMINISTRATION, COMPRISING AN ACTIVE SUBSTANCE AND A CYCLODEXTRIN

(75) Inventors: Domenico Fanara, Wanze (BE); Monique Berwaer, Ham-sur-Heure-Nalinnes (BE); Philippe Nolf, Brussels (BE); Henri Vranckx, Brussels (BE); Michel Deleers, Linkebeek (BE)

(73) Assignee: UCB, S.A., Brussels (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,735

(22) PCT Filed: Jul. 2, 1998

(86) PCT No.: PCT/BE98/00100

§ 371 (c)(1),
(2), (4) Date: Dec. 23, 1999

(87) PCT Pub. No.: WO99/01133

PCT Pub. Date: Jan. 14, 1999

(30) Foreign Application Priority Data

Jul. 3, 1997 (BE) .............................. 9700572

(51) Int. Cl.⁷ .......................................... A61K 31/4965
(52) U.S. Cl. ................................. 514/255.04; 514/58
(58) Field of Search ................................. 514/255.04

(56) References Cited

U.S. PATENT DOCUMENTS

| 4,525,358 A | 6/1985 | Baltes et al. ............... 514/255 |
| 5,244,881 A | 9/1993 | Coutel-Egros ............. 514/58 |
| 5,419,898 A | * 5/1995 | Ikejiri et al. ............. 424/78.04 |
| 5,866,179 A | 2/1999 | Testa ....................... 426/3 |

FOREIGN PATENT DOCUMENTS

| EP | 0 058 146 A | 8/1982 |
| EP | 0 605 203 A | 7/1994 |
| JP | 60-204712 | 10/1985 |

OTHER PUBLICATIONS

Becirevic, M et al., "Improvement of in vitro dissoultion characteristic of meclozine hydrochloride by cyclodextrin complexation", Abstract to Pharmazie (Germany), vol. 47, pp. 202–204, Mar. 1992.*
Abstract to JP 05036412, May 31, 1993.*
Database WPI, Week 8551, Derwent Publications, Ltd.; London, GB; AN 85–319295, XP002058687, see Abstract & JP 60 204712 A (SS Pharmaceutical KK) Oct. 16, 1985.
Becirevic et al., Pharmazie 47, pp. 202–204 (1992).

* cited by examiner

Primary Examiner—Dwayne C. Jones
(74) Attorney, Agent, or Firm—Wenderoth, Lind & Ponack, L.L.P.

(57) ABSTRACT

The invention concerns pharmaceutical compositions for oral administration, comprising an active substance belonging to the family of substituted benzhydrylpiperazines and at least a cyclodextrin.

18 Claims, No Drawings

PHARMACEUTICAL COMPOSITIONS FOR ORAL ADMINISTRATION, COMPRISING AN ACTIVE SUBSTANCE AND A CYCLODEXTRIN

This application is a 371 of PCT/BE98/00100, filed Jul. 2, 1998.

The present invention relates to pharmaceutical compositions for oral administration, comprising an active substance belonging to the substituted benzhydrylpiperazine family and a cyclodextrin.

Many substances belonging to the substituted benzhydrylpiperazine family are known as being substances which have advantageous pharmacological properties.

For example, GB patent 817,231 in the name of the Applicant describes substituted benzhydryl-piperazines corresponding to the general formula

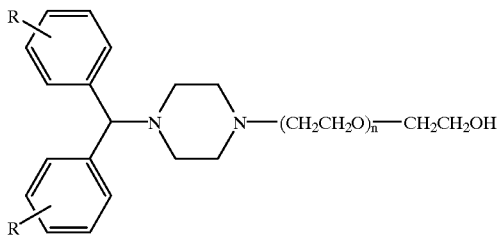

in which R and $R^1$ represent, independently of each other, a hydrogen or halogen atom, or an alkyl or alkoxy group, where R and $R^1$ can be in an ortho, meta or para position, and n represents the number 1 or 2, as well as the pharmaceutically acceptable salts thereof.

Among these compounds is found, in particular, 2-[2-[4-[(4-chlorophenyl)phenylmethyl]-1-piperazinyl]-ethoxy] ethanol, also known as hydroxyzine, and the dihydrochloride thereof, which are well known for their antihistaminic and tranquilizing properties.

Patent EP 58146 in the name of the Applicant describes substituted benzhydrylpiperazines corresponding to the general formula

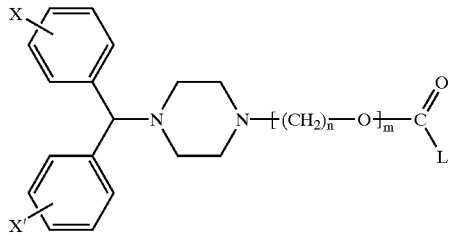

in which L represents an —OH or —$NH_2$ group, X and X', taken individually, represent a hydrogen atom, a halogen atom, a linear or branched $C_1$ or $C_4$ alkoxy radical or a trifluoromethyl radical, m is equal to 1 or 2 and n is equal to 1 or 2, as well as the pharmaceutically acceptable salts thereof.

Among these compounds, 2-[2-[4-[(4-chlorophenyl) phenylmethyl]-1-piperazinyl]acetic acid, also known as cetirizine and the dihydrochloride thereof are well known for their antihistaminic properties.

Hitherto, the only commercial pharmaceutical compositions for oral administration containing compounds of this type are of conventional type. In the case of film-coated tablets, administration takes place by swallowing by means of the simultaneous absorption of liquid. When the absorption needs to take place without simultaneous absorption of liquid (pre- or postoperative conditions, absence of drinking water, etc.), a conventional mode of administration is unsuitable on account of the extremely bitter taste of these substituted benzhydrylpiperazines.

Various techniques intended to mask the taste of pharmaceutical substances have been described.

For example, U.S. Pat. No. 3,558,600 describes a method for masking the bitter taste of antihistaminic agents belonging to the substituted 1-(p-chloro-benzhydryl)piperazine family, which consists in converting the active substance in free base form into the form of its salt with a long-chain alkyl sulfate, for example such as stearyl sulfate.

Another known method for masking the taste of active principles consists in forming an inclusion complex between the active principle and a cyclodextrin. In this case, the masking of the taste arises from the trapping of the active principle which cannot be released as it passes through the mouth. However, this solution to the problem of masking the taste entails another problem specific to the masking of the taste of orally administered pharmaceutically active substances, namely the problem of the bioavailability and speed of action of the active principle. Specifically, if the association constant of the inclusion complex is too large, there is a risk that the active principle will not be released easily enough to allow good absorption in the gastrointestinal tract. In this case, the expected therapeutic effect cannot be obtained.

Patent EP 399,902 mentions this twofold problem intrinsic to pharmaceutical compositions for oral administration, namely the masking of taste combined with good bioavailability. That patent describes freeze-dried and porous pharmaceutical forms comprising, besides the conventional excipients and additives for this type of formulation, the active principle and a cyclodextrin, as well as processes for preparing these pharmaceutical forms. Pharmaceutical compositions containing the following active principles are described in the embodiment examples of the invention: ketoprofen, trimipramine methanesulfonate, zopiclone, phenobarbital, vitamin A, lemon essence, pritinamycin or vitamin D3.

However, that document does not make it possible to conclude that the masking of taste and the bioavailability of these active principles are indeed obtained in all cases. In the case of pharmaceutical substances belonging to the substituted benzhydryl-piperazine family, this problem is of special importance since, although it is desirable to mask the extremely bitter, unpleasant taste of these active principles, it is also essential that they should be released immediately after administration in order to obtain a rapid and efficient effect.

The Applicant thus set itself the aim of searching for novel pharmaceutical compositions which allow easier oral administration of pharmaceutical substances belonging to the substituted benzhydryl-piperazine family than is possible with the current compositions, while still ensuring good bioavailability of the active substance.

We have just discovered novel pharmaceutical forms for oral administration which make it possible both to efficiently mask the taste of substances belonging to the substituted benzhydrylpiperazine family and to obtain good bioavailability of these compounds when they are administered orally, even without liquid being taken simultaneously. In particular, the Applicant set itself the aim of searching for such formulations which are in the form of chewable tablets, dry syrups, granules or sublingual tablets.

Accordingly, the present invention relates to orally administrative solid pharmaceutical compositions comprising an active substance belonging to the substituted benzhydrylpiperazine family and at least one cyclodextrin.

The cyclodextrins which can be used according to the present invention can be chosen from α, β or γ cyclodextrins, or from alkyl or hydroxyalkyl derivatives thereof, such as heptakis(2,6-di-o-methyl)-β-cyclodextrin (commonly abbreviated to DIMEB), randomly methylated β-cyclodextrin (commonly abbreviated to RAMEB) and hydroxypropyl β-cyclodextrin (commonly abbreviated to HPβCD).

Among the active substances belonging to the substituted benzhydrylpiperazine family which will be mentioned in particular are 2-[2-[4-[(4 -chlorophenyl)phenylmethyl]-1-piperazinyl]ethoxy]acetic acid (cetirizine), 2-[2-[4-[(4-chlorophenyl)phenylmethyl]-1-piperazinyl]ethoxy]ethanol (hydroxyzine), 2-[2-[4-[bis(4-fluorophenyl)methyl]-1-piperazinyl]ethoxy]acetic acid (efletirizine), 1-(4-chlorophenyl)phenylmethyl]-4-[(3-methylphenyl)methyl]piperazine (meclizine) or 1-[(4-tert-butylphenyl)methyl]-4-[(4-chlorophenyl)phenylmethyl]piperazine (buclizine), the optically active isomers thereof and the pharmaceutically acceptable salts thereof.

The pharmaceutical compositions according to the present invention can be in various orally-administrable forms. In particular, the pharmaceutical compositions according to the present invention can be in the form of dry syrups, chewable tablets, granules or sublingual tablets which are particularly suitable for oral administration without simultaneous absorption of liquid.

The excipients used are the conventional excipients used for compositions of this type.

In the case of dry syrups and granules, diluents such as polyols (mannitol, sorbitol, sucrose, etc.) and flavorings can be used, for example.

In the case of chewable tablets, any conventional excipient which gives good tabletting parameters can be used, such as diluents (mannitol, sorbitol, etc.), crumbling agents or swelling agents (polyvinylpolypyrrolidone, sodium croscarmellose, starches and derivatives, cellulose and derivatives, etc.), lubricants (magnesium stearate, etc.), flow agents (Aerosil 200, etc.) and flavorings.

In the case of sublingual tablets, the excipients cited above can be used, selecting those which are water-soluble.

As regards the preparation methods, any common method used by pharmacists for the preparation of compositions of this type can be used.

If so desired, the complex of the active substance with cyclodextrin can be prepared beforehand, for example by blending the active substance and the cyclodextrin in the presence of water or by preparing an aqueous solution containing the active substance and the cyclodextrin in the desired molar ratio.

Alternatively, the active substance and the cyclodextrin can be simply mixed together with the other excipients and adjuvants.

The examples which follow illustrate the present invention without limiting it. In these examples, the parts are expressed on a weight basis.

EXAMPLE 1

Bitterness Test

Varicus solutions are prepared by adding β-cyclodextrin to a solution of 2 mg/ml of cetirizine dihydrochloride such that the molar ratio between the β-cyclodextrin and the cetirizine is respectively 0, 0.5, 1.0, 2.0 and 4.0.

The bitterness of these solutions was tested on a group of 7 individuals. The results of this test are given in Table 1.

TABLE 1

| | Bitterness test | | | | |
|---|---|---|---|---|---|
| | Molar ratio | | | | |
| β-CD/cetirizine | 0.0 | 0.5 | 1.0 | 2.0 | 4.0 |
| Absence of bitterness | 0 | 0 | 0 | 3 | 7 |
| Very faintly bitter | 0 | 1 | 6 | 4 | 0 |
| Strongly bitter | 7 | 6 | 1 | 0 | 0 |

A reduction in the bitterness of cetirizine dihydrochloride is noted when β-cyclodextrin is added to the cetirizine dihydrochloride solution. This reduction is particularly noticeable when the molar ratio between the β-cyclodextrin and the cetirizine dihydrochloride is between 1.0 and 4.0.

EXAMPLE 2

Solubility Test

The solubility of hydrophobic molecules in water is increased in the presence of cyclodextrins, as regards both the rate of dissolution and the amount of active substance dissolved. Modification of the solubility in water of a hydrophobic active substance in the presence of cyclodextrin thus constitutes a method commonly used for demonstrating the formation of an inclusion complex (see J. Szetli, in V. F. Smolen and L. A. Ball, Controlled Drug Bioavailability, Vol. 3, Wiley, New York (1985), 365–420).

Although cetirizine dihydrochloride is very soluble in water at neutral pH, its solubility is much lower when the pH is between 2.5 and 3.5 (solubility of about 1 g/100 ml). In this test, the modification of the solubility of cetirizine dihydrochloride in water at pH 3.4 in the presence of β-cyclodextrin was examined, in order to demonstrate the formation of an inclusion complex between cetirizine and β-cyclodextrin.

Two solutions A and B were prepared. Solution A contained cetirizine dihydrochloride in water at pH 3.4; solution B contained cetirizine dihydrochloride and β-cyclodextrin in a 1:1 molar ratio in water at pH 3.4. These two solutions were stirred at room temperature until thermodynamic equilibrium was reached.

After stirring, only a very small amount of cetirizine (1 g/100 ml of water) could be dissolved in solution A. On the other hand, solution B allowed 27 g/100 ml of cetirizine to be dissolved in the aqueous phase.

Moreover, β-cyclodextrin is sparingly soluble in water (1.85 g/100 ml). Its solubility increases gradually as cetirizine dihydrochloride is added, up to a 1:1 β-cyclodextrin/cetirizine molar ratio. At pH 3.4, the solubility of β-cyclodextrin increases by a factor of at least 30.

EXAMPLE 3

Demonstration of the Formation of a Complex by UV Spectroscopy

The complexation of a host with a cyclodextrin is generally reflected by a slight displacement of the absorption maximum in UV spectroscopy and/or by a change in the molar extinction coefficient (J. Szetli in Cyclodextrin Technology, Chapter 2.2.4.2, Kluwer Academic Publishers, 1988).

Various solutions containing various molar ratios of cetirizine dihydrochloride/β-cyclodextrin were prepared and the differences in absorbence at 230 nm were determined. The reason for this is that, in water, cetirizine has an absorption maximum at 230 nm in the absence of cyclodextrin.

A decrease in the absorbence at the absorption maximum gradually as the β-cyclodextrin concentration increases is observed. This hypochromatic effect indicates the formation of an inclusion complex.

EXAMPLE 4

Competition for the Complexation with Colored Indicators

In this example, changes in the absorption spectrum in the visible range of a solution containing a complex between a cyclodextrin and a colored indicator when cetirizine is introduced into the solution are observed. In this case, the cetirizine comes into competition with the colored indicator for the formation of an inclusion complex. The changes in the visible-range spectrum thus make it possible to determine whether or not cetirizine forms an inclusion complex with cyclodextrin.

Two acid-base indicators were used; crystal violet and methyl orange. In the case of the acid-base indicators, the changes in the absorption spectrum due to complexation with a cyclodextrin are often large given that the complexation brings about a change in the pK of the indicator. If the pH of the solution is close to the pK, the addition of a cyclodextrin to an acid-base indicator solution brings about ionization or deionization of the indicator, which is reflected by a change in the color of the solution. Consequently, the absorption maximum in the visible spectrum is displaced as a function of the degree of complexation.

When cetirizine dihydrochloride is introduced into an aqueous solution containing an acid-base indicator and β-cyclodextrin, a displacement of the absorption maximum is also observed, indicating thereby that some of the indicator is no longer complexed with the β-cyclodextrin. This means that some of the β-cyclodextrin has been used to complex the cetirizine introduced into the medium. (J. Szetli in Cyclodextrin Technology, Chapter 2.2.4.1, Kluwer Academic Publishers, 1988).

An average value for the association constant of 3292 $mol^{-1}$ for the competition with crystal violet, and of 3587 $mol^{-1}$ for the competition with methyl orange, are determined.

EXAMPLE 5

Identification of the Formation of a Complex by Proton NMR

Nuclear magnetic resonance (NMR) spectroscopy is commonly used to demonstrate the formation of inclusion complexes with cyclodextrins (F. Djedaini and B. Perly in D. Duchene, New Trends in Cyclodextrin and Derivatives, Chap. 6, §2&3, Edition de Santé, Paris 1991, F. Djedaini et al., J. Pharm. Sciences, 79 (7), 643–646 (1990)).

In this test, various solutions containing variable molar ratios of β-cyclodextrin/cetirizine dihydrochloride in a 9:1 $H_2O/D_2O$ mixture were analyzed by proton NMR spectroscopy. The observed regions of the spectrum correspond to the resonant frequency zone for protons 2 to 6.6' (d=3.0 to 4.0 ppm) of β-cyclodextrin and to the resonant frequency zone of the aromatic protons of cetirizine (d=7.2 to 7.6 ppm).

Only one resonance peak at an average resonant frequency between the resonant frequency of the free molecule and that of the complexed molecule is observed for each proton. This means that the system analyzed is in an exchange regime which is faster than the time scale of the NMR measurement.

When the amount of cetirizine present in solution with the β-cyclodextrin increases, a large shift upfield is observed for the protons located inside the hydrophobic cavity of β-cyclodextrin (protons 3 and 5). On the other hand, the resonant frequencies of the protons located on the outside of the β-cyclodextrin cavity (protons 2 and 4) hardly shift at all. This clearly demonstrates the formation of an inclusion complex in the β-cyclodextrin cavity.

As regards the protons of cetirizine, it is found that only the aromatic protons undergo a shift in their resonant frequency. The full interpretation is complicated by the overlapping of the resonance signals of the 9 aromatic protons. This observation indicates the inclusion of the aromatic portion of cetirizine in the β-cyclodextrin cavity.

In addition, the stoichiometric coefficient for the complex was determined by the technique of continuous variation, also known as the "Job method" (see F. Djedaini et al., J. Pharm. Sciences, 79 (7), 643–646 (1990), P. Job, Ann. Chim., 9, 113–134 (1928)). Variation of the chemical shift for proton 3 of β-cyclodextrin was taken as variable. By this method, it is determined that the complex formed has a 1:1 stoichiometry.

EXAMPLE 6

Chewable Polyol-based Cetirizine Tablets

Cetirizine dihydrochloride (10 parts) and β-cyclodextrin (55 parts) are blended in the presence of water in a planetary mixer for 20 minutes. In this way, the complex between the cetirizine dihydrochloride and the β-cyclodextrin is formed. This mixture is then dried in an oven.

After drying, the complex is mixed with the following excipients: Sorbitol (29.45 parts), Acesulfam K (0.7 parts) Aerosil 200 (0.3 parts), Croscarmellose sodium (2.1 parts), Glycamil (1.2 part), liquorice flavoring (0.25 part).

The mixture is then tabletted in a conventional manner.

EXAMPLE 7

Polyol-free Chewable Cetirizine Tablets

The cetirizine dihydrochloride and β-cyclodextrin complex is prepared in the same way as in Example 6. The excipients used are as follows: Polyvinylpolypyrrolidone (35 parts), Avicel pH 101 (50 part), Avicel CE 15 (7 parts), Aerosil 200 (1 part), magnesium stearate (1.6 parts), Acesulfam K (1.4 part), flavorings (2.7 parts).

EXAMPLE 8

Dry Cetirizine Syrup

Two compositions A and B were prepared by mixing together the ingredients given in the table:

| Constituent (in parts) | A | B |
| --- | --- | --- |
| Cetirizine dihydrochloride | 5 | 10 |
| β-cyclodextrin | 27.5 | 55 |
| Flavoring | 0.5 | 0.5 |
| Mannitol | qs 1000 | qs 1000 |

The mixture is granulated with water in a planetary mixer and then extruded. The extrudate obtained is dried on a fluidized-air bed.

EXAMPLE 9

Hydroxyzine Granules

A composition C was prepared by mixing together the ingredients given in the table:

| Constituent (in parts) | C |
| --- | --- |
| Hydroxyzine dihydrochloride | 25 |
| β-cyclodextrin | 142 |
| Flavoring | 2 |
| Impalpable sucrose | qs 1000 |

The mixture is granulated with water in a planetary mixer and then extruded. The extrudate is dried in a fluidized-air bed.

What is claimed is:

1. A solid pharmaceutical composition for oral administration comprising a mixture of an active substance belonging to the substituted benzhydrylpiperazine family, an optically active isomer thereof or a pharmaceutically active salt thereof and at least one cyclodextrin, wherein said mixture does not contain any inclusion complexes.

2. Pharmaceutical composition according to claim 1, wherein it is in the form of a chewable tablet, a dry syrup, granules or a sublingual tablet.

3. Pharmaceutical composition according to claim 1, characterized in that the active substance is chosen from the group consisting of cetirizine, hydroxyzine, efletirizine, meclizine and buclizine, the optically active isomers thereof and the pharmaceutically acceptable salts thereof.

4. Pharmaceutical composition according to claim 1, characterized in that the cyclodextrin is chosen from the group consisting of α, β or γ cyclodextrins and alkyl or hydroxyalkyl derivatives thereof.

5. Pharmaceutical composition according to claim 1, the molar ratio between the cyclodextrin and the active substance is between 1.0 and 4.0.

6. Pharmaceutical composition according to claim 1, wherein the cyclodextrin is heptakis(2,6-di-o-methyl)-β-cyclodextrin, randomly methylated β-cyclodextrin or hydroxylpropyl β-cyclodextrin.

7. A method of making a solid pharmaceutical composition for oral administration comprising a mixture of an active substance belonging to the substituted benzhydrylpiperazine family, an optically active isomer thereof or a pharmaceutically active salt thereof and at least one cyclodextrin, wherein said mixture does not contain any inclusion complexes, comprising:

provinding an active substance from the substituted benzhydrylpiperazine family, an optically active isomer thereof or a pharmaceutically active salt thereof and at least one cyclodextrin;

b) mixing said active substance and said at least one cyclodextrin to form a mixture, wherein said mixture does not contain any inclusion complexes;

c) optionally adding to said mixture at least one non-complexing excipient or adjuvent; and d) drying said mixture to form a solid pharmaceutical composition.

8. The method of claim 7, wherein the pharmaceutical composition is in the form of a chewable tablet, a dry syrup or a sublingual tablet.

9. The method of claim 7, wherein the active substance is chosen from the group consisting of cetirizine, hydroxyzine, efletirizine, meclizine and buclizine, the optically active isomers thereof and the pharmaceutically acceptable salts thereof.

10. The method of claim 7, wherein the cyclodextrin is chosen from the group consisting of α, β or γ cyclodextrins and alkyl or hydroalkyl derivatives thereof.

11. The method of claim 7, wherein the molar ratio between the cyclodextrin and the active substance is between 1.0 and 4.0.

12. The method of claim 7, wherein the cyclodextrin is heptakis(2,6-di-o-methyl)-β-cyclodextrin, randomly methylated β-cyclodextrin or hydroxylpropyl β-cyclodextrin.

13. A method for orally administering an active substance belonging to the substituted benzhydrylpiperazine family, an optically active isomer thereof or a pharmaceutically active salt thereof comprising:

orally administering a solid pharmaceutical composition comprising a mixture of an active substance belonging to the substituted benzhydrylpiperazine family, an optically active isomer thereof or a pharmaceutically active salt thereof and at least one cyclodextrin, wherein said mixture does not contain any inclusion complexes.

14. The method of claim 13, wherein the pharmaceutical composition is in the form of a chewable tablet, a dry syrup or a sublingual tablet.

15. The method of claim 13, wherein the active substance is chosen from the group consisting of cetirizine, hydroxyzine, efletirizine, meclizine and buclizine, the optically active isomers thereof and the pharmaceutically acceptable salts thereof.

16. The method of claim 13, wherein the cyclodextrin is chosen from the group consisting of α, β or γ cyclodextrins and alkyl or hydroalkyl derivatives thereof.

17. The method of claim 13, wherein the molar ratio between the cyclodextrin and the active substance is between 1.0 and 4.0.

18. The method of claim 13, wherein the cyclodextrin is heptakis(2,6-di-o-methyl)-β-cyclodextrin, randomly methylated β-cyclodextrin or hydroxylpropyl β-cyclodextrin.

* * * * *